United States Patent [19]

Pruett et al.

[11] 4,133,776

[45] Jan. 9, 1979

[54] MANUFACTURE OF POLYFUNCTIONAL COMPOUNDS

[75] Inventors: Roy L. Pruett; Wellington E. Walker, both of Charleston, W. Va.

[73] Assignee: Union Carbide Corporation, New York, N.Y.

[21] Appl. No.: 842,366

[22] Filed: Oct. 14, 1977

Related U.S. Application Data

[60] Continuation of Ser. No. 666,613, Mar. 15, 1976, abandoned, which is a continuation of Ser. No. 470,114, May 15, 1974, abandoned, which is a division of Ser. No. 219,130, Jan. 19, 1972, Pat. No. 3,833,634, which is a continuation-in-part of Ser. No. 210,538, Dec. 21, 1971, abandoned.

[51] Int. Cl.$^2$ .................. B01J 31/20; B01J 31/22; B01J 31/24
[52] U.S. Cl. .................. 252/431 N; 252/431 R; 252/431 C; 252/443
[58] Field of Search ........... 252/431 R, 431 C, 431 N, 252/443

[56] References Cited

U.S. PATENT DOCUMENTS

| | | | |
|---|---|---|---|
| 3,081,357 | 3/1963 | Alderson et al. | 252/443 X |
| 3,417,088 | 12/1968 | Kmiecik | 252/443 X |
| 3,511,885 | 5/1970 | Hughes | 252/431 R X |
| 3,536,692 | 10/1970 | Otsuka et al. | 252/431 N X |
| 3,558,517 | 1/1971 | Hughes et al. | 252/431 C X |
| 3,646,079 | 2/1972 | Lawrenson | 252/431 R X |
| 3,660,493 | 5/1972 | Johnson et al. | 252/431 C X |
| 3,689,533 | 9/1972 | Schultz | 252/431 N X |

*Primary Examiner*—Patrick Garvin
*Attorney, Agent, or Firm*—Bernard Lieberman

[57] ABSTRACT

A catalyst composition useful in the process for the preparation of polyfunctional oxygen-containing compounds such as ethylene glycol and/or derivatives thereof which comprise reacting an oxide of carbon with hydrogen using a rhodium complex catalyst.

9 Claims, No Drawings

MANUFACTURE OF POLYFUNCTIONAL COMPOUNDS

This application is a continuation of our prior U.S. application Ser. No. 666,613, filed Mar. 15, 1976, now abandoned, which is a continuation of application Ser. No. 470,114, filed May 15, 1974, now abandoned, which is a division of application Ser. No. 219,130, filed Jan. 19, 1972, now U.S. Pat. No. 3,833,634, issued Sept. 3, 1974, and which is a continuation-in-part of application Ser. No. 210,538, filed Dec. 21, 1971, now abandoned.

This invention relates to the synthesis of polyfunctional oxygen-containing organic compounds. In one aspect the invention is directed to the preparation of polyhydric alcohols such as ethylene glycol and/or derivatives thereof by the reaction of mixtures comprising hydrogen and an oxide of carbon as reactants.

It is known that monofunctional compounds such as methanol can be obtained by reaction between carbon monoxide and hydrogen at elevated pressures, e.g., up to about 1000 atmospheres, and temperatures ranging from 250° C. to 500° C., using mixtures of copper, chromium and zinc oxides as the catalyst therefor. It is disclosed in U.S. Pat. No. 2,451,333 that polyhydroxy compounds are produced by reaction of formaldehyde, carbon monoxide, and hydrogen in the presence of hydrogenation catalysts. It has also been reported that formaldehyde can be produced by reaction between carbon monoxide and hydrogen at elevated pressures but repeated attempts to carry out this synthesis of formaldehyde have invariably failed to yield any substantial quantity of the desired product. It is generally recognized that the previously disclosed processes for the synthesis of formaldehyde from carbon monoxide and hydrogen at high pressures are either completely inoperative or else give rise to insignificantly small quantities of formaldehyde.

In British Pat. No. 655,237, published July 11, 1951, there is disclosed the reaction between carbon monoxide and hydrogen at elevated pressures and temperatures, e.g., above 1500 atmospheres at temperatures up to 400° C., using certain hydrogenation catalysts as exemplified by cobalt-containing compounds. U.S. Pat. No. 2,636,046 is substantially similar in its disclosure re the above said British patent since both are presumably derived from a common parent United States application and both are assigned to a common assignee. The only catalysts employed in the operative examples of said U.S. Pat. No. 2,636,046 are those which contain cobalt.

It is also well-known that nickel is predominantly a catalyst for synthesis and for reforming methane according to the reaction

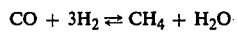

which proceeds from left to right at temperatures below about 500° C. and in the opposite direction at higher temperatures; see Kirk-Othmer, Encyclopedia of Chemical Technology, Second Edition, Volume 4, pages 452–453, John Wiley and Sons, New York (1964).

Quite unexpectedly and unobviously, indeed, we have discovered a novel process for the preparation of polyfunctional oxygen-containing organic compounds and/or derivatives thereof by the hydrogenation of an oxide of carbon using rhodium complex compounds as the catalysts therefor. By the practice of suitable embodiments of the invention there can be prepared polyfunctional oxygen-containing organic compounds which comprise predominant amounts of ethylene glycol and lesser amounts of oxygenated products such as methyl acetate, glycerol, methanol, ethanol, and/or propylene glycol, etc. Moreover, the novel process proceeds in the substantial absence of the methanation reaction. Attempts to produce formaldehyde by the novel process have not been successful. As will be apparent from the operative Examples herein, the use of compounds such as lead acetate, zinc oxide, stannous acetate, triruthenium dodecacarbonyl, palladium acetylacetonate, platinum acetylacetonate, cupric acetate, tetrairidium dodecacarbonyl, mixture of chromium hexacarbonyl and manganese decacarbonyl, etc., failed to produce polyfunctional products such as ethylene glycol by the reaction between carbon monoxide and hydrogen at about 230° C. under a pressure of approximately 25,000 psia.

The present invention thus provides, in the practice of a desirable embodiment, a novel route for synthesizing polyhydric alcohols and or derivatives thereof from carbon monoxide and hydrogen in accordance with the following equation:

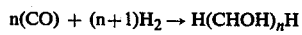

wherein n is an integer greater than one, desirably from 2 to 3. In a preferred embodiment, the novel process can be effected in the presence of various normally-liquid organic diluents and mixtures of diluents. These diluents can be inert under the operative conditions of the process, or they may be reactive. Such diluents can comprise organic ligands hereinafter described in detail. In a further preferred embodiment the novel process is effected at relatively low pressures heretofore not attainable in the synthesis of polyhydric compounds such as ethylene glycol and/or derivatives thereof directly from the reaction between carbon monoxide and hydrogen as reactants.

In their active forms, the catalysts which are suitable in the practice of the invention comprise rhodium in complex combination with carbon monoxide without/without additional ligands described hereinafter and mixtures thereof. Active species can comprise rhodium in complex combination with carbon monoxide and hydrogen. Active species can also comprise a complex catalyst mixture in which the available "complexing sites" of rhodium are occupied, through coordination bonding, with at least one or two and even upwards to three organic ligands described hereinafter. One and upwards to three, and desirably one or two, carbon monoxide ligands, also satisfy "complexing sites" of rhodium through coordination bonding. Active rhodium complexes can also contain hydrogen as a ligand together with the carbon monoxide and the organic ligands. Though we do not wish to be held to any theory or mechanistic discourse, the ultimate composition of the active complex catalyst can be likened or attributable to the outcome of competing reactions among the aforesaid ligands for "complexing sites" with rhodium. Such competing reactions can be influenced or varied, to a certain extent, by the choice of organic ligand, by the choice of normally-liquid organic diluent, by the partial pressures exerted by hydrogen and/or carbon monoxide and other factors. As a generalized statement, therefore, the component, e.g., carbon monoxide, hydrogen, and/or organic ligand which can shift the equilibrium of the competing reaction in its favor should enjoy the greater opportunities of occupying the "complexing sites" or forming coordination bonds with rhodium.

As used in this specification, including the claims, the term "complex" means a coordination compound formed by the union of one or more electronically rich molecules or atoms capable of independent existence with one or more electronically poor molecules or atoms, each of which is also capable of independent existence.

Organic ligands which are suitable in the practice of the invention contain at least one nitrogen atom (hereinafter called Lewis base nitrogen atom) and/or at least one oxygen atom (hereafter called Lewis base oxygen atom), said atoms possessing a pair of electrons available for the formation of coordinate bonds with rhodium. Desirably, the organic ligand contains at least two Lewis base nitrogen atoms, or at least two Lewis base oxygen atoms, or at least one Lewis base nitrogen atom plus at least one Lewis base oxygen atom, said atoms possessing a pair of electrons available for the formation of coordinate bonds with rhodium, and said organic ligand forming with rhodium a chelate structure. Suitable chelate structures contain from 4 to 6 atoms in the "ring". Preferably the "ring" is composed of the Lewis base atoms, carbon, and rhodium. In suitable embodiments the organic ligands contain from 2 and upwards to 4 Lewis base atoms, preferably from 2 to 3 such atoms, and most preferably 2 Lewis base atoms. These organic ligands are said to be multidentate or polydentate, that is to say, such ligands are bidentate, tridentate, or quadridentate, depending on whether 2, 3, or 4 Lewis base atoms are involved in the formations of chelate structures with rhodium.

Organic ligands which contain at least one Lewis base nitrogen atom will oftentimes hereinafter be referred to as "organic nitrogen ligands"; those ligands which contain at least one Lewis base oxygen atom will oftentimes be referred to as "organic oxygen ligands"; and those which contain at least one Lewis base nitrogen atom plus at least one Lewis base oxygen atom will oftentimes be referred to as "organic aza-oxa ligands".

Suitable organic nitrogen ligands most generally contain carbon, hydrogen, and nitrogen atoms. Suitable organic oxygen ligands most generally contain carbon, hydrogen, and oxygen atoms. Suitable organic aza-oxa ligands most generally contain carbon, hydrogen, oxygen, and nitrogen atoms. The carbon atoms can be acyclic and/or cyclic such as aliphatic, cycloaliphatic, aromatic (including fused and bridged) carbon atoms, and the like. Preferably, the organic ligands contain from 2 to 20 carbon atoms. The nitrogen atoms can be in the form of imino (—N=), amino

nitrilo (N≡), etc. Desirably, the Lewis base nitrogen atoms are in the form of imino nitrogen and/or amino nitrogen. The oxygen atoms can be in the form of groups such as hydroxyl (aliphatic or phenolic), carboxyl

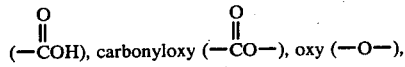

-continued

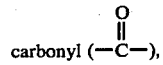

etc., all of said groups containing Lewis base oxygen atoms. In this respect, it is the "hydroxyl" oxygen in the

group and the "oxy" oxygen in the

group that are the Lewis base atoms. The organic ligands may also contain other atoms and/or groups such as alkyl, cycloalkyl, aryl, chloro, thiaalkyl, trialkylsilyl, and the like.

The following are merely illustrations of various organic ligands which can form with rhodium the chelate structure shown below:

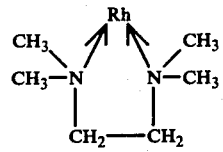

N,N,N',N'-tetramethylethylenediamine ligand

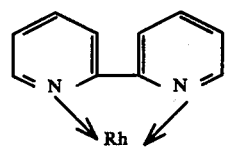

2,2'-dipyridyl ligand

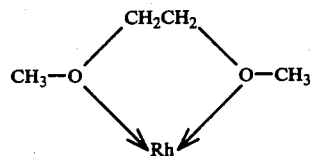

1,2-dimethoxyethane ligand

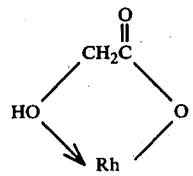

glycolic acid ligand

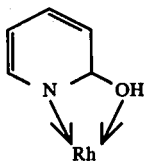

2-hydroxypyridine ligand

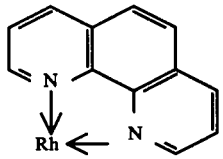

1,10-phenanthroline ligand

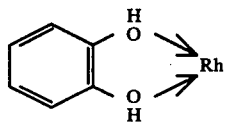

pyrocatechol ligand

It should be recognized that the chelate structures illustrated above are incomplete in that other ligands, for example, carbon monoxide and/or hydrogen, satisfy the "complexing sites" of rhodium.

Illustrative organic nitrogen ligands include for instance, N,N,N',N'-tetramethylethylenediamine, N,N,N',N'-tetraethylethylenediamine, N,N,N',N'-tetra-n-propylethylenediamine, N,N,N',N'-tetramethylmethylenediamine, N,N,N',N'-tetraethylmethylenediamine, N,N,N',N'-tetraisobutylmethylenediamine, piperazine, N-methylpiperazine, N-ethylpiperazine, 2-methyl-N-methylpiperazine, 2,2'-dipyridyl, methyl-substituted 2,2'-dipyridyl, ethyl-substituted 2,2'-dipyridyl, 1,4-diazabicyclo[2.2.2]octane, methyl-substituted 1,4-diazabicyclo[2.2.2]octane, purine, 2-aminopyridine, 2-(dimethylamino)pyridine, 1,10-phenanthroline, methyl-substituted 1,10-phenanthroline, 2-(dimethylamino)-6-methoxyquinoline, 7-chloro-1,10-phenanthroline, 4-triethylsilyl-2,2'-dipyridyl, 5-(thiapentyl)-1,10-phenanthroline, tri-n-butylamine, and the like.

Illustrative organic oxygen ligands include, by way of illustrations, glycolic acid, methoxyacetic acid, ethoxyacetic acid, diglycolic acid, thiodiglycolic acid, diether ether, tetrahydrofuran, dioxane, tetrahydropyran, pyrocatechol, citric acid, 2-methoxyethanol, 2-ethoxyethanol, 2-n-propoxyethanol, 2-n-butylethanol, 1,2,3-trihydroxybenzene, 1,2,4-trihydroxybenzene, 2,3-dihydroxynaphthalene, cyclohexane-1,2-diol, oxetane, 1,2-dimethoxybenzene, 1,2-diethoxybenzene, methyl acetate, ethanol, 1,2-dimethoxyethane, 1,2-diethoxyethane, 1,2-di-n-propoxyethane, 1,2-di-n-butoxyethane, pentane-2,4-dione, hexane-2,4-dione, heptane-3,5-dione, octane-2,4-dione, 1-phenylbutane-1,3-dione, 3-methylpentane-2,4-dione; the mono- and dialkyl ethers of propylene glycol, of diethylene glycol, of dipropylene glycol; and the like.

Illustrative organic aza-oxa ligands include, for example, ethanolamine, diethanolamine, isopropanolamine, di-n-propanolamine, N,N-dimethylglycine, N,N-diethylglycine, iminodiacetic acid, N-methyliminodiacetic acid, N-methyldiethanolamine, 2-hydroxypyridine, methyl-substituted 2-hydroxypyridine, picolinic acid, methyl-substituted picolinic acid, nitrilotriacetic acid, 2,5-dicarboxypiperazine, N-(2-hydroxyethyl)iminodiacetic acid, ethylenediaminetetraacetic acid, 2,6-dicarboxypyridine, 8-hydroxyquinoline, 2-carboxyquinoline, cyclohexane-1,2-diamine-N,N,N',N'-tetraacetic acid, the tetramethyl ester of ethylenediaminetetraacetic acid, and the like.

In the practice of preferred embodiments of the invention a normally-liquid organic diluent is employed. Such diluents can be inert organic diluents, or they may be reactive diluents, and they can include the aforedescribed organic ligands, or mixtures thereof. Illustrative of the normally-liquid organic diluents which are generally suitable in the practice of desirable embodiments of the invention include, for example, saturated and aromatic hydrocarbons, e.g., hexane, octane, dodecane, naphtha, decalin, tetrahydronaphthalene, kerosene, mineral oil, cyclohexane, cycloheptane, alkylcycloalkane, benzene, toluene, xylene, naphthalene, alkylnaphthalene, etc.; ethers such as tetrahydrofuran, tetrahydropyran, diethyl ether, 1,2-dimethoxybenzene, 1,2-ethoxybenzene, the mono- and dialkyl ethers of ethylene glycol, of propylene glycol, of butylene glycol, of diethylene glycol, of dipropylene glycol, of dibutylene glycol, of oxyethyleneoxypropylene glycol, etc.; carboxylic acids such as acetic acid, propionic acid, butyric acid, caproic acid, stearic acid, benzoic acid, cyclohexanecarboxylic acid, etc.; alkanols such as methanol, ethanol, propanol, isobutanol, 2-ethylhexanol, etc.; ketones such as acetone, methyl ethyl ketone, cyclohexanone, cyclopentanone, etc.; esters such as methyl acetate, ethyl acetate, propyl acetate, butyl acetate, methyl propionate, ethyl butyrate, methyl laurate, etc.; water; anhydrides such as phthalic anhydride, acetic anhydride, etc.; and others. Tetrahydrofuran and dioxane are preferred diluents. It should be noted that the use of reactive diluents in the practice of desirable embodiments of the invention can give rise to a range of useful products. For instance, the mono- and diacetate esters of ethylene glycol can be obtained by using acetate acid as the diluent in the reaction medium. The use of alkanols, e.g., methanol and ethanol, can result in the monoalkyl ethers of ethylene glycol.

Either heterogeneous or homogeneous reaction mixtures may be employed in the practice of the invention. In preferred embodiments, rhodium complex catalysts which are soluble in the reaction medium give outstanding results. However, the synthesis of polyfunctional products and/or derivatives thereof can be suitably effected by using catalysts which are not homogeneously distributed throughout the reaction mixture. Solid catalysts which remain in place during the course of the reaction may be employed satisfactorily. Suspensions of liquid or solid catalysts in liquid or gaseous media may be employed. In suitable embodiments of the invention the rhodium complex compound can be used in combination with inert materials or contained or deposited on porous supports such as alumina, silica-alumina, silica gel, activated charcoal, titania, zirconia, zeolites as well as the zeolitic molecular sieves, pumice, kieselguhr, inert porous organic polymers, and the like.

The active forms of the rhodium complex compounds may be prepared by various techniques. They can be performed and then introduced into the reaction zone. Alternatively, any of the host of rhodium-containing substances as well as the organic ligand can be introduced into the reaction zone and, under the operative conditions of the process (which of course includes hydrogen and carbon monoxide), the active rhodium complex species can be generated in situ. Illustrative of rhodium-containing substances which can be conveniently introduced or placed in the synthesis zone include, for example, rhodium oxide ($Rh_2O_3$), tetrarhodium dodecacarbonyl, dirhodium octacarbonyl, hexarhodium hexadecacarbonyl ($Rh_6(CO)_{16}$), rhodium(II) formate, rhodium(II) acetate, rhodium(II) propionate, rhodium(II) butyrate, rhodium(II) valerate, rhodium(III) naphthenate, rhodium dicarbonyl acetylacetonate, rhodium tris(acetylacetonate), rhodium trihydroxide, indenylrhodium dicarbonyl, rhodium dicarbonyl (1-phenylbutane-1,3-dione), rhodium tris(acetylacetonate), tris(hexane-2,4-dionato)rhodium(III), tris(heptane-2,4-dionato)rhodium(III), tris(1-phenylbutane-1,3-dionato)rhodium(III), tris(3-methylpentane-2,4-dionato)rhodium(III), tris(1-cyclohexylbutane-1,3-dionato)rhodium(III), finely divided rhodium metal, rhodium metal and rhodium-containing compounds deposited on porous supports or carriers such as those exemplified previously, and others.

The quantity of catalyst employed is not narrowly critical and can vary over a wide range. In general, the novel process is desirably conducted in the presence of a catalytically effective quantity of the active rhodium species which gives a suitable and reasonable reaction rate. Reaction proceeds when employing as little as about $1 \times 10^{-6}$ weight percent, and even lesser amounts, of rhodium (calculated as the metal in the complex catalyst) based on the total quantity of reaction mixture. The upper concentration limit can be quite high, e.g., about one weight percent rhodium, and higher. The upper limit appears to be dictated and controlled more by economics in view of the exceedingly high cost of rhodium metal and rhodium compounds. No particular advantages at the relatively high concentrations of rhodium are manifest. Depending on various factors such as the organic ligand of choice, the partial pressures of carbon monoxide and hydrogen, the total operative pressure of the system, the operative temperature, the choice of the normally-liquid organic diluent, and other considerations, a catalyst concentration of from about $1 \times 10^{-5}$ to about $1 \times 10^{-1}$ weight percent rhodium (contained in the complex catalyst) based on the total quantity of reaction mixture, is generally suitable in the practice of the invention.

The operative temperature which may be employed can vary over a wide range of elevated temperatures. In general, the novel process can be conducted at a temperature in the range of from about 100° C. and upwards to approximately 375° C., and higher. Operative temperatures outside this stated range, though not excluded from the scope of the invention, do not fall within certain desirable embodiments of the invention. At the lower end of the temperature range, and lower, the rate of reaction to desired product becomes markedly slow. At the upper temperature range, and beyond, signs of some catalyst instability become manifest. Notwithstanding this factor, reaction continues and polyfunctional compounds and/or derivatives are produced. Additionally, one should take notice of the equilibrium reaction for forming ethylene glycol:

$$2 CO + 3H_2 \rightleftharpoons HOCH_2CH_2OH$$

At relatively high temperatures the equilibrium increasingly favors the left hand side of the equation. To drive the reaction to the formation of increased quantities of ethylene glycol, higher partial pressures of carbon monoxide and hydrogen are required. Processes based on correspondingly higher operative pressures, however, do not represent preferred embodiments of the invention in view of the high investment costs associated with erecting chemical plants which utilize high pressure utilities and the necessity of fabricating equipment capable of withstanding such enormous pressures. Suitable operative temperatures can be between about 125° C. to about 350° C., and desirably from about 150° C. to about 325° C. A preferred temperature range is from about 160° C. to about 300° C.

The novel process is suitably effected over a wide superatmospheric pressure range. At pressures below about 500 psia, the rate of desired product formation is quite slow, and consequently, relatively faster reaction rates and/or higher conversions to the desired product can be obtained by higher operative pressures, e.g., at a pressure of at least about 800 psia. Pressures as high as 50,000 psia, and higher, can be employed but with no apparent advantages attendant thereto especially to offset the unattractive plant investment outlay. In one embodiment of the invention, the upper pressure limitation is approximately 25,000 psia. Effecting the novel process below about 14,000 psia, especially below about 6,000 psia, results in cost advantages which are associated with low pressure quipment requirements. A suitable pressure range is from about 1000 psia to about 12,000 psia, preferably from about 1500 psia to about 6000 psia. The pressures referred to above represent the total pressure of hydrogen and carbon monoxide. In a preferred embodiment of the invention, rhodium complex catalyst is maintained in solution in the liquid reaction medium. In addition to the partial pressure exerted by carbon monoxide and by hydrogen, a partial pressure will also be exerted by inert gases, e.g., nitrogen, if employed in the reaction.

The novel process is effected for a period of time sufficient to produce the desired polyfunctional oxygen-containing products and/or derivatives thereof. In general, the residence can vary from minutes to several hours, e.g., from a few minutes to approximately 24 hours, and longer. It is readily appreciated that the residence period will be influenced, to a significant extent, by the reaction temperature, the concentration and choice of the complex catalyst, the total gas pressure and the partial pressure exerted by its components, the concentration and choice of diluent, and other factors. The synthesis of the desired product(s) by the reaction of hydrogen with an oxide of carbon is suitably conducted under operative conditions which give reasonable reaction rates and/or conversions.

The relative amounts of carbon monoxide and hydrogen which are initially present in the reaction mixture can be varied over a wide range. In general, the mol ratio of $CO:H_2$ is in the range of from about 20:1 to about 1:20, suitably from about 10:1 to about 1:10, and preferably from about 5:1 to about 1:5. It is to be understood, however, that molar ratios outside the aforestated broad range may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention. For instance, polyfunctional products comprising glycol and/or derivatives thereof are obtained by using mixtures containing carbon dioxide and hydrogen. Mixtures of carbon dioxide, carbon monoxide and hydrogen can also be employed. If desired, the reaction mixture can comprise steam and carbon monoxide.

The novel process can be executed in a batch, semi-continuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal and/or external heat exchanger(s) to thus control undue temperature fluctuations, or to prevent any possible "runaway" reaction temperatures due to the exothermic nature of the reaction. In preferred embodiments of the invention, agitation means to vary the degree of mixing the reaction mixture can be suitably employed. Mixing induced by vibration, shaker, stirrer, rotatory, oscillation, ultrasonic, etc., all illustrative of the types of agitation means which are contemplated. Such means are available and well-known to the art. Catalyst may be initially introduced into the reaction zone batchwise, or it may be continuously or intermittently introduced into such zone during the course of the synthesis reaction. Means to introduce and/or adjust the reactants, either intermittently or continuously, into the reaction zone during the course of the reaction can be conveniently utilized in the novel process especially to maintain the desired molar ratios of and the partial pressures exerted by the reactants.

As intimated previously, the operative conditions can be adjusted to optimize the conversion of the desired product and/or the economics of the novel process. In a continuous process, for instance, when it is preferred to operate at relatively low conversions, it is generally desirable to recirculate unreacted synthesis gas with-/without make-up carbon monoxide and hydrogen to the reactor. Recovery of the desired product can be achieved by methods well-known in the art such as by distillation, fractionation, extraction, and the like. A fraction comprising rhodium catalyst, generally contained in byproducts and/or normally-liquid organic diluent, can be recycled to the reaction zone, if desired. All or a portion of such fraction can be removed for recovery of the rhodium values or regeneration to the active rhodium species, if necessary. Fresh rhodium catalyst can be intermittently added to the recycle stream or directly to the reaction zone.

In one aspect the invention is directed to the preparation of novel compositions which comprise rhodium in complex combination with carbon monoxide and various organic ligands exemplified previously with/without hydrogen. In suitable embodiments of this aspect of the invention the novel complex compounds comprise rhodium in complex combination with carbon monoxide and organic ligands and optionally hydrogen, said organic ligands having at least two Lewis base atoms, desirably two to four such atoms, and preferably two such atoms, each of which possesses a pair of electrons available for the formation of coordinate bonds with rhodium, said atoms being oxygen and/or nitrogen, and said organic ligands forming with rhodium a chelate structure which contains from 4 to 6 atoms therein (including rhodium); with the proviso that said organic ligands do not include 1,3-diketone compounds. Most desirably, the chelate structure or "ring" is composed of rhodium, carbon atoms, and two Lewis base atoms which can be oxygen and/or nitrogen, said oxygen being in the form of groups such as oxy (—O—), carbonyloxy

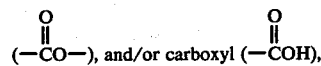

(—CO—), and/or carboxyl (—COH), and said nitrogen being in the form of imino (—N—) and/or amino

especially tertiary amino. Preferably the organic ligands consist essentially of carbon, hydrogen, and oxygen atoms, or carbon, hydrogen, and nitrogen atoms, or carbon, hydrogen, oxygen, and nitrogen atoms. The carbon atoms can be acyclic or/and cyclic such as aliphatic, cycloaliphatic, aromatic (including fused and bridged) carbon atoms. Useful organic ligands contain from 4 to 20 carbon atoms.

In another aspect of the invention the novel rhodium complex compounds can be represented by the following formula:

wherein H, CO, and L are ligands, and wherein x, y, and z are integers. More specifically H represents hydrogen; CO represents carbon monoxide; x is an integer having a value of zero or one; y is an integer having a value of 1 to 3, preferably 1 to 2; z is an integer having a value of 1 to 3, preferably 1 to 2, and most preferably z equals one; the sum of x + y + z equals 3 to 5, preferably 3; and L represents an organic ligand illustrated previously, with the proviso that L does not include 1,3-diketones. Illustrative complexes include, by way of illustrations:

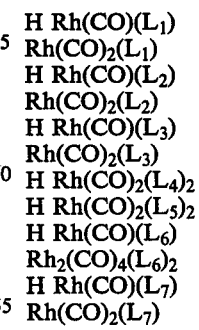

wherein $L_1$ represents pyrocatechol;
wherein $L_2$ represents 2-hydroxypyridine;
wherein $L_3$ represents picolinic acid;
wherein $L_4$ represents dioxane;
wherein $L_5$ represents tetrahydrofuran;
wherein $L_6$ represents 2,2'-dipyridyl;
wherein $L_7$ represents 1,10-phenanthroline; and the like.

The novel rhodium complex compounds can be most suitably prepared as a dispersion or as a solution. The novel rhodium complex compounds can be combined with or deposited on porous carriers or supports. Several of the normally-liquid organic diluents illustrated previously can be used to prepare such dispersions or solutions. The carriers or supports have likewise been exemplified previously. The preparation of the novel rhodium complex compounds is conveniently carried out in a diluent or mixture of diluents, e.g., benzene. Tetrarhodium dodecacarbonyl, though of limited solubility, can be added to the diluent in a finely divided form. Any of several of the rhodium-containing compounds illustrated previously can be employed in lieu of $Rh_4(CO)_{12}$. Organic ligand such as 2-hydroxypyridine is also added therein. The complexing reaction can be effected under a carbon monoxide pressure of about 2 to 15 atmospheres, and higher, using a temperature of about 30° C. to about 100° C., for a period of time ranging from minutes to a few days, generally from about 30 minutes to about 24 hours. The resulting rhodium complex contained in the organic diluent is catalytically active in the novel process. This complex consists essentially of rhodium in complex combination with carbon monoxide and the organic ligand of choice. By following the same procedure as above but conducting the reaction under a carbon monoxide and hydrogen pressure (molar ratios of $CO:H_2$ suitably ranging from about 0.5:1 to about 3:1), it is generally more desirable to employ a slightly higher temperature range, e.g., about 50°–150° C., and higher, and a total pressure ranging from about 2 to 30 atmospheres, and higher. In this instance the complex consists essentially of rhodium in complex combination with carbon monoxide, hydrogen, and the organic ligands. In preparing the aforesaid complex compounds, one can suitably employ from about 0.5 to about 2 moles of organic ligand per mole of rhodium (contained in the rhodium compound used as a rhodium source). Ratios outside this stated range can be employed especially when it is desirable to use diluent quantities of the organic ligand. Infrared analysis of the thus prepared rhodium complex compounds confirms the presence of coordination bonds between rhodium and carbonyl, rhodium and organic ligand, etc.

Solutions of the novel catalytically active rhodium complex compounds can be deposited on porous carriers or supports of the type illustrated previously. For example, the catalytically active solution can be poured on the carrier, or the carrier can be immersed in an excess of the liquid solution, with the excess being subsequently removed. The impregnated support or carrier is then maintained at a temperature sufficient to volatilize the diluent to permit drying of the impregnated carrier. A vacuum may also be applied.

In the following illustrative Examples, the term "parts" designates parts by weight (in grams). The term "efficiency" was determined as follows:

$$\text{Efficiency (\%)} = \frac{\text{Grams of polyhydric Alcohol Product Produced}}{\text{Grams of Liquid Oxygenated Products Produced}} \times 100$$

EXAMPLE 1

A 100 ml. capacity stainless-steel reactor capable of withstanding pressures up to 7000 atmospheres was charged with 0.52 part of rhodium dicarbonyl acetylacetonate dissolved in 45 parts of tetrahydrofuran. The reactor was sealed and charged with 1300 atmospheres of synthesis gas (mixture of hydrogen and carbon monoxide, molar ratio $H_2:CO = 1:1$). Heat was applied to the reactor and contents, when the temperature of the mixture inside the reactor reached 190° C., as measured by a suitably placed thermocouple, an additional 100 atmospheres of synthesis gas ($H_2:CO = 1:1$) was added. This addition was repeated at 200°, 210° and 220° C. At a reaction temperature of 230° C. additional synthesis gas was added until the pressure reached 3,400 atmospheres.

The temperature was maintained at 230° for a period of 4.5 hours. During this period of time additional synthesis gas was added whenever the total pressure dropped to 2,900 atmospheres; the amount of synthesis gas ($H_2:CO = 1:1$) added was sufficient to bring the total pressure to 3,400 atmospheres. Several such repressurizations were required.

After the 4.5-hour period, the vessel and contents were cooled to room temperature. The excess gases were vented, and the reaction product mixture was removed. It measured 58 parts. Analysis by vapor phase chromatography proved the presence of 9.8 parts of ethylene glycol, 1.5 parts of propylene glycol, 1.5 parts of glycerine, along with methanol, water, and methyl formate. The efficiency to polyhydric compounds was 64%.

EXAMPLE 2

A 10-ml. stainless-steel reactor, fitted with an internal thermocouple and attached to a rocker, was charged with 5.0 parts of water, 0.2 part of isopropanol and 0.13 part of rhodium dicarbonyl acetylacetonate. The reactor was charged with 2700 atmospheres of synthesis gas (molar ratio $H_2:CO = 1:1$) and heat was applied. At a temperature of 100° C., rocking was begun. The vessel and contents were maintained at 250° C. for 1.5 hours. During this period of time the pressure was maintained in the region of 2400–3000 atmospheres by periodic repressurizing with synthesis gas ($H_2:CO = 1:1$).

The vessel and contents were cooled and the excess gases were vented. The product contained ethylene glycol and propylene glycol.

EXAMPLE 3

A 10-ml. stainless-steel reactor was charged with 4.5 parts of tetrahydrofuran and 0.13 parts of rhodium dicarbonyl acetylacetonate. The reaction was conducted as described in Example 2 except that the temperature was 225° C. and the reaction time was one hour and ten minutes.

The product, 7.0 parts, was shown by vapor phase chromatography to contain 1.3 parts of ethylene glycol.

EXAMPLE 4

A 100-ml. stainless-steel reactor was charged with 40 parts of methanol, 4 parts of toluene and 0.65 part of rhodium dicarbonyl acetylacetonate. The reactor was sealed and the reaction was conducted as described in Example 1 except that the reaction temperature was 250° C. The product contained 4.3 parts of ethylene glycol.

EXAMPLE 5

A 100-ml. stainless-steel reactor was charged with 40 parts of isopropanol and 0.65 part of rhodium dicarbonyl acetylacetonate. The reaction was conducted as described in Example 1 except that the reaction temperature was 250° C. The product, 53 parts, was shown to contain 3.6 parts of ethylene glycol.

EXAMPLE 6

A 100-ml. stainless-steel reaction vessel, capable of withstanding pressures of 7000 atmospheres, was charged with 40 parts of ethanol and 0.65 part of rhodium dicarbonyl acetylacetonate. The reaction was conducted as described in Example 1, except that the reaction temperature was 250° C. and the time of heating was 3.5 hours. The product was shown to contain ethylene glycol and minor amounts of ethylene glycol monoethyl ether.

EXAMPLE 7

A 10-ml. stainless-steel reactor was charged with 5.5 parts of tetrahydrofuran and 1.0 part of 1% rhodium on alumina. The reactor was charged with 1500 atmospheres of synthesis gas (molar ratio $H_2:CO = 1:1$) and heat was applied. At 100° C., rocking was begun. The vessel and contents were maintained at a temperature of 230° C. and a pressure range of 1300–1700 atmospheres for 4 hours. Periodic addition of synthesis gas ($H_2:CO = 1:1$) was required to maintain the required pressure.

The vessel and contents were cooled to ambient temperature. The excess gases were vented and the product was removed. Analysis showed the presence of 0.28 part of ethylene glycol.

EXAMPLE 8

A 10-ml. vessel was charged with 5.5 parts of tetrahydrofuran and 0.12 part of stannous acetate. The reaction was conducted as described in Example 7, except that the heating period was 2 hours. The product contained no polyhydric alcohols.

EXAMPLE 9

A 10-ml. reaction vessel was charged with 5.5 parts of tetrahydrofuran and 0.07 part of triruthenium dodecacarbonyl. The reaction was conducted as in Example 8. The product contained no polyhydric alcohols.

EXAMPLE 10

A 10-ml. reaction vessel was charged with 5.5 parts of tetrahydrofuran and 0.075 part of palladium (II) acetylacetonate. The reaction was conducted as described in Example 8. The product contained no polyhydric alcohols.

EXAMPLE 11

A 10-ml. reaction vessel was charged with 5.5 parts of tetrahydrofuran and 0.10 part of platinum (II) acetylacetonate. The reaction was conducted as described in Example 8. The product contained no polyhydric alcohols.

EXAMPLE 12

A 10-ml. reaction vessel was charged with 5.5 parts of tetrahydrofuran and 0.025 part of cupric acetate. The reaction was conducted as described in Example 8. The product contained no polyhydric alcohols.

EXAMPLE 13

A 10-ml. reactor was charged with 5.5 parts of tetrahydrofuran, 0.055 part of chromium hexacarbonyl and 0.049 part of dimanganese decacarbonyl. The reaction was conducted as described in Example 8. Analysis of the product showed no detectable amounts of polyhydric alcohols.

EXAMPLE 14

A 10-ml. reactor was charged with 5.5 parts of tetrahydrofuran and 0.027 part of tetrairidium dodecacarbonyl. The reaction was conducted as described in Example 8. Analysis of the product showed that the iridium did not catalyze the formation of polyhydric alcohols.

EXAMPLE 15

A 10-ml. stainless-steel reactor was charged with 6.0 parts of water and 0.04 part of zinc oxide. The reaction was conducted as described in Example 8. The product contained no polyhydric alcohols.

EXAMPLE 16

A 10-ml. stainless-steel reactor was charged with 6.0 parts of acetic acid and 0.2 part of lead tetraacetate. The reaction was conducted as described in Example 8. No polyhydric alcohols were detected in the product mixture.

EXAMPLE 17

A 10-ml. stainless-steel reaction vessel was charged with 6.0 parts of acetic acid and 0.043 part of dicobalt octacarbonyl. The reaction was conducted as described in Example 8. The product contained no ethylene glycol but traces of the mono- and diacetate of ethylene glycol were detected.

EXAMPLE 18

A 10-ml. reaction vessel was charged with 4.5 parts of N-methyl-2-pyrrolidinone and 0.13 part of rhodium dicarbonyl acetylacetonate. The reaction was conducted as described in Example 2. The product contained substantial quantities of ethylene glycol.

EXAMPLE 19

A 10-ml. stainless-steel reactor, fitted with an internal thermocouple and attached to a rocker, was charged with 5.5 parts of tetrahydrofuran, 0.10 part of rhodium dicarbonyl acetonylacetonate and 0.22 part of pyrocatechol. The reactor was sealed, charged with 400 atmospheres of synthesis gas (molar ratio $H_2:CO = 1:1$) and heat was applied. At a temperature of 100° C., rocking was begun. The temperature was maintained at 180° C. for 20 hours. The pressure was maintained at 700–750 atmospheres by periodic addition of synthesis gas.

The vessel and contents were cooled to room temperature and the excess gases were vented. The product was analyzed by vapor phase chromatography and proved to contain significant quantities of ethylene glycol.

EXAMPLE 20

A 10-ml. stainless-steel reaction vessel was charged with 5.5 parts of tetrahydrofuran, 0.13 part of rhodium dicarbonyl acetylacetonate and 0.11 parts of pyrocatechol. The reaction was conducted as described in Example 8. Analysis of the reaction product mixture showed that 0.50 part of ethylene glycol was produced.

EXAMPLE 21

A 10-ml. stainless-steel reaction vessel was charged with 4.5 parts of dioxane, 0.8 part of toluene and 0.13 part of rhodium dicarbonyl acetylacetonate. The reaction was conducted as described in Example 2, except that the pressure was maintained at 2700–3300 atmospheres.

The product, 7.5 parts, was analyzed and found to contain 0.73 part of ethylene glycol.

EXAMPLE 22

A stainless-steel reactor of 100-ml. capacity was charged with 54.6 parts of o-dimethoxybenzene (veratrole) and 0.65 part of rhodium dicarbonyl acetylacetonate. The reaction was conducted as described in Example 5. The product was removed (70 parts) and analyzed. 5.1 parts of ethylene glycol were present.

EXAMPLE 23

A 10-ml. reaction vessel was charged with 5 parts of tetraethylene glycol dimethyl ether and 0.13 part of rhodium dicarbonyl acetylacetonate. The reaction was conducted as described in Example 2. The product, 7.5 parts, was analyzed by vapor phase chromatography and found to contain 1.25 parts of ethylene glycol.

EXAMPLE 24

A 10-ml. reactor was charged with 4.5 parts of dioxane, 0.9 part of toluene and 1.0 part of 5% by weight rhodium on carbon. The reaction was conducted as described in Example 2. The reaction product contained substantial quantities of ethylene glycol and propylene glycol.

EXAMPLE 25

A 100-ml. stainless-steel reactor capable of withstanding pressures up to 7000 atmospheres was charged with 45 parts of tetrahydrofuran, 0.65 part of rhodium dicarbonyl acetylacetonate and 0.78 part of 2,2'-bipyridyl. The reactor was sealed and charged with 1300 atmospheres of synthesis gas (molar ratio $H_2:CO = 1:1$). Heat was applied to the reactor and contents. When the temperature inside the reactor reached 190° C., as measured by a suitably placed thermocouple, an additional 100 atmospheres of synthesis gas ($H_2/CO = 1:1$) was added. This addition was repeated at 200° C., 210° C., and 222° C. At a reaction temperature of 230° C., additional synthesis gas was added until the pressure reached 3,400 atmospheres.

The temperature was maintained at 230° C. for a period of 4.5 hours. During this period of time, additional synthesis gas was added whenever the total pressure dropped to 2900 atmospheres. The amount of synthesis gas ($H_2/CO = 1:1$) added was sufficient to bring the total pressure to 3,400 atmospheres. Several such repressurizations were required.

After the 4.5-hour period, the reactor and contents were cooled to room temperature. The excess gases were vented, and the reaction product mixture was removed. It measured 64 parts. Analysis by vapor phase chromatography proved the presence of 7.5 parts of ethylene glycol, 1.8 parts of propylene glycol, 2.0 parts of glycerine along with water, methanol, ethanol and methyl formate. The efficiency to polyhydric alcohols was 60%. Analysis of the unreacted, excess gases by mass spectrographic procedures proved the absence of any significant quantity of methanol as a byproduct.

EXAMPLE 26

A 100-ml. stainless-steel reactor was charged with 45 parts of tetrahydrofuran, 0.65 part of rhodium dicarbonyl acetylacetonate and 0.43 part of piperazine. The reaction was conducted as described in Example 24. The reaction product mixture, 60 parts, contained 8.6 parts of ethylene glycol, 1.7 parts of propylene glycol, and 2.0 parts of glycerine.

EXAMPLE 27

A 10-ml. stainless-steel reactor, fitted with an internal thermocouple and attached to a rocker, was charged with 5.5 parts of tetrahydrofuran, 0.13 part of rhodium dicarbonyl acetylacetonate and 0.144 part of 8-aminoquinoline. The reactor was charged with 1100 atmospheres of synthesis gas (molar ratio $H_2:CO = 1:1$) and heat was applied. At a temperature of 100° C., rocking was begun. The vessel and contents were maintained at 230° C. for two hours. During this time the pressure was maintained in the region of 1300–1700 atmospheres by periodic repressurizing with synthesis gas ($H_2:CO = 1:1$).

The vessel and contents were cooled to room temperature. The excess gases were vented and the reaction product mixture was removed (6.5 parts). Analysis showed the presence of ethylene glycol in substantial quantity and traces of propylene glycol.

EXAMPLE 28

A reaction is conducted as in Example 27, except that the organic nitrogen ligand employed is 1,10-phenanthroline. Substantial quantities of ethylene glycol are produced.

EXAMPLE 29

A 10-ml. reaction vessel was charged with 5.5 parts of tetrahydrofuran, 0.13 part of rhodium dicarbonyl acetylacetonate and 0.09 part of 2-aminopyridine. The reaction was conducted as described in Example 27. The product contained ethylene glycol in substantial quantities (35% efficiency, based on carbon).

EXAMPLE 30

A 10-ml. reaction vessel was charged with 5.5 parts of N,N,N',N'-tetramethylmethylenediamine and 0.050 part of rhodium dicarbonyl acetylacetonate. The reaction was conducted as described in Example 27. The product contained 0.2 part of ethylene glycol.

EXAMPLE 31

A 10-ml. reaction vessel was charged with 5.5 parts of tetrahydrofuran, 0.13 part of rhodium dicarbonyl acetylacetonate and 0.12 part of N,N,N',N'-tetramethylethylenediamine. The reaction was conducted as described in Example 3. The product was analyzed and found to contain 0.64 part of ethylene glycol.

EXAMPLE 32

A 100-ml. stainless-steel reactor was charged with 36 parts of dioxane, 9 parts of toluene, 0.8 part of pyridine and 1.3 parts of rhodium dicarbonyl acetylacetonate. The reaction was conducted as described in Example 4. The product (67 parts) contained 4.4 parts of ethylene glycol and a significant quantity of propylene glycol. The unreacted gases were analyzed by mass spectrographic means and proved to contain no significant quantity of methane.

EXAMPLE 33

A 100-ml. stainless-steel reactor was charged with 0.13 part of rhodium dicarbonyl acetylacetonate, 0.10 part of 2-hydroxypyridine and 45 parts of tetrahydrofuran. The reaction was conducted as described in Example 4. The product was analyzed and found to contain 6.3 parts of ethylene glycol, 2.5 parts of propylene glycol and 5.0 parts of glycerine. The efficiency to polyhydric alcohols was 92%.

EXAMPLE 34

A 100-ml. stainless steel reactor was charged with 22.5 parts of tetrahydrofuran, 0.73 part of 8-hydroxyquinoline and 0.65 part of rhodium dicarbonyl acetylacetonate. The reaction was conducted as described in Example 4. The product contained 14.4 parts of ethylene glycol, 6.7 parts of propylene glycol and 4.3 parts of glycerine. The efficiency to polyhydric alcohols was 85%.

EXAMPLE 35

A 100-ml. stainless-steel reactor was charged with 45 parts of tetrahydrofuran, 0.65 part of rhodium dicarbonyl acetylacetonate and 0.84 part of pyridine-2,6-dicarboxylic acid. The reaction was conducted as described in Example 4. The product contained 8.6 parts of ethylene glycol, 1.7 parts of propylene glycol and 2.8 parts of glycerine.

EXAMPLE 36

A 10-ml. reaction vessel was charged with 5.5 parts of tetrahydrofuran, 0.19 part of 8-hydroxyquinoline and 0.13 part of rhodium dicarbonyl acetylacetonate. The reaction was conducted as described in Example 27. The product contained substantial quantities of ethylene glycol and small quantities of propylene glycol and glycerine.

EXAMPLE 37

A 10-ml. reaction vessel was charged with 5.5 parts of tetrahydrofuran, 0.13 part of rhodium dicarbonyl acetylacetonate and 0.19 part of nitrilotriacetic acid. The reaction was conducted as in Example 27. The product contained substantial quantities of ethylene glycol and a trace of propylene glycol.

EXAMPLE 38

A 10-ml. reaction vessel was charged with 5.5 parts of tetrahydrofuran, 0.13 part of rhodium dicarbonyl acetylacetonate and 0.29 part of ethylenediamine-tetraacetic acid. The reaction was conducted as described in Example 27. Ethylene glycol was produced in 60% efficiency.

EXAMPLE 39

A ten-ml. stainless-steel reaction vessel was charged with 5.5 parts of tetrahydrofuran, 0.11 part of rhodium dicarbonyl acetylacetonate and 0.18 part of 2-hydroxypyridine. The reactor was pressurized with 500 atmospheres of synthesis gas (molar ratio $H_2:CO = 1:1$) and heat was applied. At 100° C., rocking was begun. The vessel and contents were maintained at a temperature of 230° C. and a pressure of 820–880 atmospheres for a period of 2 hours. Periodic addition of synthesis gas ($H_2:CO = 1:1$) was required to maintain the required pressure.

The vessel and contents were cooled to ambient temperature. The excess gases were vented and the product was removed. Analysis proved the presence of substantial quantities of ethylene glycol.

EXAMPLE 40

A 10-ml. stainless-steel reaction vessel was charged with 6.0 parts of N,N'-dimethylethanolamine and 0.05 part of rhodium dicarbonyl acetylacetonate. The reaction was conducted in a manner similar to that described in Example 27. The product was analyzed and found to contain significant quantities of ethylene glycol.

EXAMPLE 41

A 100-ml. stainless-steel reaction vessel was charged with 23.4 parts of tetrahydrofuran, 24.0 parts of water, 0.21 part of rhodium dicarbonyl acetylacetonate and 0.19 part of 2-hydroxypyridine. The reaction was conducted in a manner similar to that described in Example 1. The product (52 parts) was analyzed by vapor phase chromatography and found to contain substantial quantities of ethylene glycol.

EXAMPLE 42

A 10-ml. reaction vessel was charged with 6.0 parts of N-methylmorpholine, 0.05 part of rhodium dicarbonyl acetylacetonate and 0.10 part of 2-hydroxypyridine. The reaction was conducted in a manner similar to that described in Example 27. The product contained substantial quantities of ethylene glycol and a smaller amount of propylene glycol.

EXAMPLE 43

A 10-ml. reaction vessel was charged with 6.0 parts of N-methylmorpholine and 0.05 part of rhodium dicarbonyl acetylacetonate. The reaction was conducted in a manner similar to that described in Example 27. The product contained substantial quantities of ethylene glycol and a smaller amount of propylene glycol.

EXAMPLE 44

A 100-ml. reaction vessel was charged with 45.0 parts of tetrahydrofuran, 0.65 part of rhodium dicarbonyl acetylacetonate and 2.2 parts of pyrocatechol. The reaction was conducted in a manner similar to that described in Example 1. The liquid product mixture was analyzed and found to contain 11.9 parts of ethylene glycol. The unreacted gases were analyzed by mass spectrographic means and found to contain no significant quantity of methane.

EXAMPLE 45

A 250-ml. stainless-steel vessel equipped with stirring was charged with 90 parts of tetrahydrofuran, 1.3 parts of rhodium dicarbonyl acetylacetonate and 1.9 parts of 2-hydroxypyridine. The vessel is sealed, flushed with synthesis gas and pressurized with synthesis gas to 300 atmospheres (molar ratio $H_2:CO = 1:1$). Heat was applied and stirring begun. The temperature was maintained at 180° C. for 41.5 hours. The pressure was maintained between 390 and 450 atmospheres by periodic addition of synthesis gas ($H_2:CO = 1:1$) as required.

The vessel and contents were cooled to room temperature and the excess gases were vented. The product, 96 parts, was removed and analyzed by vapor phase chromatography. Significant quantities of ethylene glycol were found to be present.

EXAMPLE 46

A 100-ml. stainless-steel reaction vessel was charged with 36 parts of tetrahydrofuran, 10 parts of morpholine and 0.65 part of rhodium dicarbonyl acetyl acetonate. The reaction was conducted in a manner similar to that described in Example 1. The product, 62 parts, contained substantial quantities of ethylene glycol and propylene glycol.

EXAMPLE 47

A 10-ml. reaction vessel was charged with 5.5 parts of tetrahydrofuran, 0.13 part of rhodium dicarbonyl acetylacetonate and 0.19 part of nitrilotriacetic acid. The reaction was conducted in a manner similar to that described in Example 27. The product contained substantial quantities of ethylene glycol.

EXAMPLE 48

A 100-ml. stainless-steel reaction vessel was charged with 45 parts of tetrahydrofuran, 0.65 part of rhodium dicarbonylacetylacetonate and 0.65 part of pyridine-2-carboxylic acid. The reaction was conducted in a manner similar to that described in Example 1. The product amounted to 57 parts, of which 10.9 parts were ethylene glycol. Analysis of the unreacted gases proved the absence of any significant quantity of methane.

EXAMPLE 49

A 100-ml. stainless-steel vessel was charged with 48 parts of methanol. 0.52 part of rhodium dicarbonyl acetylacetonate and 0.73 part of 8-hydroxyquinoline. The reaction was conducted in a manner similar to that described in Example 1. The product, 66 parts, contained 6.9 parts of ethylene glycol. The unreacted gas contained no significant quantity of methane.

EXAMPLE 50

A 100-ml. stainless-steel vessel was charged with 36 parts of dioxane, 9 parts of toluene, 1.3 parts of rhodium dicarbonyl acetylacetonate and 1.1 parts of triethylenediamine. The reaction was conducted as described in Example 2. The product mixture contained substantial quantities of ethylene glycol.

EXAMPLE 51

A 10-ml. reaction vessel was charged with 5.5 parts of toluene and 0.2 part of rhodium dicarbonyl acetylacetonate. The reaction was conducted in a manner similar to that described in Example 27. The product contained ethylene glycol.

EXAMPLE 52

A 10-ml. reaction vessel was charged with 5.5 parts of ethyl acetate and 0.2 parts of rhodium dicarbonyl acetylacetonate. The reaction was conducted in a manner similar to Example 27. The product was analyzed and found to contain 0.64 part of ethylene glycol.

EXAMPLE 53

A 100-ml. stainless-steel reactor, fitted with a high-speed magnetic stirrer of the dispersator type, is charged with 25 parts of tetrahydrofuran, 1.9 parts of tetrarhodium dodecacarbonyl and 4.4 parts of pyrocatechol. The remaining free space is flushed with carbon monoxide and then pressurized with 50 atmospheres of a synthesis gas in which the molar ratio of hydrogen to carbon monoxide is 3:1. Stirring is begun and the temperature is raised to 180° C., at which point the pressure is raised to 170 atmospheres of synthesis gas composed of a 3:1 molar ratio of hydrogen to carbon monoxide. The temperature is maintained at 180° C. and the pressure at 160–180 atmospheres for a period of 48 hours. The pressure is maintained in this range by the periodic addition of synthesis gas as described above. The vessel and contents are cooled to room temperature and the excess gases are vented. The product is removed and analyzed by vapor phase chromatography. Significant quantities of ethylene glycol are produced.

EXAMPLE 54

The process of Example 53 is repeated except that the synthesis gas is composed of a 1:1 molar ratio of hydrogen to carbon monoxide. Ethylene glycol is found to be present in the reaction product mixture.

EXAMPLE 55

The process of Example 53 is repeated except that the synthesis gas is composed of a 3:1 molar ratio of carbon monoxide to hydrogen and the reaction time is 72 hours. Ethylene glycol is found to be present in the reaction product mixture.

EXAMPLE 56

Tetrarhodium dodecacarbonyl, 1.9 parts, is added to a 500-ml. stainless-steel reaction vessel, along with 100-ml. of benzene and 1.56 parts of 2,2'-dipyridyl. The vessel is sealed, flushed with carbon monoxide and pressurized with 150 psia of carbon monooxide. The vessel and contents are heated to 90° C. for 24 hours, then cooled to room temperature. The excess carbon monoxide is vented and the reaction product mixture is removed under a nitrogen atmosphere. The benzene is removed by evaporation at 30°–40° C. under a stream of nitrogen. Solid dirhodium tetracarbonyl bis(2,2'-bipyridyl) remains.

EXAMPLE 57

Tetrarhodium dodecacarbonyl, 1.9 parts, 100 ml. of benzene and 1.8 parts of 1,10-phenanthroline are placed in a 500-ml. stainless-steel reaction vessel. The vessel is sealed, flushed with carbon monoxide and pressurized with 75 psia of carbon monoxide and 90 psia of hydrogen. Rocking is begun and heat is applied. The vessel and contents are maintained at a temperature of 100° C. for 48 hours, then cooled to room temperature and vented of excess gases. The solution is removed under an atmosphere of hydrogen and found to contain hydridorhodium dicarbonyl-1,10-phenanthroline.

EXAMPLE 58

A preparation is conducted as described in Example 56, except that the ligand is o-hydroxybenzoic acid, 1.38 parts. The product is rhodium dicarbonyl o-hydroxybenzoate.

EXAMPLE 59

The process of Example 56 is repeated except that the ligand is pyridine-2-carboxylic acid, 1.23 parts. The product is rhodium dicarbonyl pyridine-2-carboxylate.

EXAMPLE 60

The process of Example 56 is repeated, except that the ligand consists of 1.45 parts of 8-hydroxyquinoline. The product is rhodium dicarbonyl 8-quinolinolate.

EXAMPLE 61

A 10-ml. reaction vessel was charged with 6 parts of acetic acid and 0.2 part of rhodium dicarbonyl acetylacetonate. The reaction was conducted as described in Example 27. The product mixture contained significant quantities of ethylene glycol.

What is claimed is:

1. The catalyst composition for preparing a polyhydric alcohol by the conversion of a mixture consisting essentially of an oxide of carbon and hydrogen to said alcohol, which catalyst is a rhodium carbonyl complex formed in the presence of said mixture at a temperature of between 100° and 375° C. and at a pressure of between 500 to 50,000 psig of said oxides of carbon and hydrogen.

2. The composition of claim 1 wherein the rhodium is complexed with a mixture of carbon monoxide, hydrogen, and an organic ligand compound, said organic ligand compound coordinates with said rhodium and contains at least one atom which possesses a pair of electrons which form a coordinate body with rhodium, which atom is at least one of Lewis base nitrogen, Lewis base oxygen and mixtures thereof and the remainder of said compound is carbon and hydrogen.

3. The composition of claim 2 wherein the Lewis base oxygen atom is one of aliphatic hydroxyl, phenolic hydroxyl, carboxyl, carbonyloxy, oxy, and carbonyl.

4. The composition of claim 2 wherein the Lewis base nitrogen is present in at least one of the forms of imino, amino or nitrilo.

5. The composition of claim 3 wherein said organic compound contains two Lewis base oxygen atoms.

6. The composition of claim 4 wherein said organic compound contains at least two Lewis base nitrogen atoms.

7. The composition of claim 2 wherein said organic compound contains at least one Lewis base oxygen atom and one Lewis base nitrogen atom.

8. The composition of claim 7 wherein said organic compound is 2-hydroxypyridine.

9. The composition of claim 7 wherein said organic compound is 8-hydroxyquinoline.

* * * * *